(12) United States Patent
Horiuchi et al.

(10) Patent No.: US 10,117,862 B2
(45) Date of Patent: *Nov. 6, 2018

(54) REMIFENTANIL INJECTION

(71) Applicant: Terumo Kabushiki Kaisha, Shibuya-ku, Tokyo (JP)

(72) Inventors: Aiko Horiuchi, Kawasaki (JP); Shigeru Suzuki, Hadano (JP)

(73) Assignee: TERUMO KABUSHIKI KAISHA, Shibuya-Ku, Tokyo (JP)

(*) Notice: Subject to any disclaimer, the term of this patent is extended or adjusted under 35 U.S.C. 154(b) by 0 days.

This patent is subject to a terminal disclaimer.

(21) Appl. No.: 15/457,142

(22) Filed: Mar. 13, 2017

(65) Prior Publication Data

US 2017/0182019 A1  Jun. 29, 2017

Related U.S. Application Data

(63) Continuation of application No. PCT/JP2014/074227, filed on Sep. 12, 2014.

(51) Int. Cl.
| | |
|---|---|
| A61K 31/445 | (2006.01) |
| A61K 31/55 | (2006.01) |
| A61K 31/4468 | (2006.01) |
| A61K 47/10 | (2017.01) |
| A61K 47/32 | (2006.01) |
| A61K 9/08 | (2006.01) |
| A61K 9/00 | (2006.01) |

(52) U.S. Cl.
CPC ........ *A61K 31/4468* (2013.01); *A61K 9/0019* (2013.01); *A61K 9/08* (2013.01); *A61K 47/10* (2013.01); *A61K 47/32* (2013.01); *A61K 31/445* (2013.01); *A61K 31/55* (2013.01)

(58) Field of Classification Search
CPC .............................. A61K 31/445; A61K 31/55
USPC ......................................... 514/329, 327, 220
See application file for complete search history.

(56) References Cited

U.S. PATENT DOCUMENTS

| | | | |
|---|---|---|---|
| 5,866,591 A | 2/1999 | Gatlin et al. | |
| 8,383,687 B2 | 2/2013 | Harris et al. | |
| 2009/0286832 A1 | 11/2009 | Nabeta et al. | |
| 2010/0069438 A1 | 3/2010 | Hickle | |

FOREIGN PATENT DOCUMENTS

| | | | |
|---|---|---|---|
| CA | 706865 A | 3/1965 | |
| JP | 34-4999 S | 6/1959 | |
| JP | 39-7787 | 5/1964 | |
| JP | 05-246891 A | 9/1993 | |
| JP | 2002-538118 A | 11/2002 | |
| JP | 2002-538119 A | 11/2002 | |
| JP | 2011520883 A | 7/2011 | |
| JP | 498009 B2 | 4/2012 | |
| WO | 2007/035573 A2 | 3/2007 | |
| WO | 2009140059 A2 | 11/2009 | |
| WO | WO-2014100624 A1 * | 6/2014 | ......... A61K 31/4468 |

OTHER PUBLICATIONS

Office Action (Notification of Reasons for Refusal) dated Sep. 27, 2016, by the Japanese Patent Office in corresponding Japanese Patent Application No. 2013-050906, and an English translation of the Office Action. (11 pgs).
Ultiva R Intravenous Dose of 2 mg, Ultiva R Intravenous Dose of 5 mg accompanying document; Janssen Pharmaceutical Kabushiki Kaisha, pp. 2-5, 2nd edition, Aug. 2009.
Shiryo, H. et al., Reference 1 Medical Incident Examples Collection Result-Medical Supplies, Ministry of Health, Labour and Welfare, The 23rd Pharmaceuticals and Medical Devices Countermeasure Subcommittee Reference Material, pp. 145-151, Sep. 20, 2012.
Tanno, M., Countermeasures against Forgetting to Dissolve Ultva TM, The Journal of Japan Society for Clinical Anesthesia, p. 1020, vol. 31 Issue 7, 2011 (month unknown).
Japan Pharmaceutical Excipients Council, Pharmaceutical Additive Handbook, Yakuji Nippo, Ltd., pp. 108-120, Feb. 28, 2007.
The thirteenth revision in the Pharmacopoeia of Japan explanatory, Hirokawa Publishing, 1996, pp. 112-128 (month unknown).
Nagata, O., "Good Practice Guide for the Use of Reminfentanil", Anesthesia 21 Century, vol. 9, No. 2-28, pp. 1652-1665, 2007 (month unknown).
Medical Journal of Kagoshima City, vol. 46, No. 6, p. 12, 2007 (month unknown).
International Search Report (PCT/ISA/210) dated Sep. 9, 2014, by the Japanese Patent Office as the International Searching Authority for International Application No. PCT/JP2014/074227.
Written Opinion (PCT/ISA/237) dated Sep. 29, 2014 by the Japanese Patent Office as the International Searching Authority for International Application No. PCT/JP2014/074227.
Extended Search Report issued by the European Patent Office in corresponding European Patent Application No. 14901745.1-1114 dated Apr. 13, 2018 (6 pages).

* cited by examiner

*Primary Examiner* — Kevin E Weddington
(74) *Attorney, Agent, or Firm* — Buchanan, Ingersoll & Rooney PC

(57) ABSTRACT

A remifentanil injection solution formulation contains remifentanil and or physiologically acceptable salts thereof, water, and a stabilizer, the remifentanil injection solution formulation contains said water at a rate of 0.007 to 0.025 mL per 1 mg of said remifentanil.

8 Claims, No Drawings

REMIFENTANIL INJECTION

TECHNICAL FIELD

The present invention relates to a remifentanil injection solution formulation. More particularly, the present invention relates to a remifentanil injection solution formulation excellent in its storage stability. The remifentanil injection solution formulation of the present invention allows remifentanil to be present therein in long-term storage.

BACKGROUND ART

An opioid analgesic has a strong analgesic action and stabilizes stress reactions of circulation dynamics caused by surgical invasion. The opioid analgesic satisfies the elements of anesthesia having sedative, analgesic, and muscle relaxant actions caused by a surgical operation and keeps stresses applied to a patient during the surgical operation to the minimum, thereby restraining the extent of the stress reactions of the circulation dynamics such as the rise of a blood pressure, tachycardia, and the like caused by the surgical stresses to the minimum. From this standpoint, the opioid analgesic is suitable as an analgesic in performing general anesthesia in that the opioid analgesic surely gives ease and comfort to a patient for her/his pain after the surgical operation is performed.

Fentanyl was used as the opioid analgesic at an anesthetizing time for the past several decades. Sufentanil and alfentanil were approved as next-generation analgesics in western countries and used as the opioid analgesic at the anesthetizing time. Under such circumstances, remifentanil was approved in October of 2006 in Japan and started to be sold from January of 2007. Currently the remifentanil is used as the opioid analgesic when general anesthesia is performed.

Fentanyl is metabolized into active and nonactive metabolites in a liver, and only 10% of the metabolites is discharged from a kidney. Thus, in a case where the fentanyl is continuously medicated, it is accumulated in a body and its action remains after the medication finishes. As a result, disease symptoms such as late-onset respiratory depression, arousal delay, nausea, and vomiting appear. On the other hand, remifentanil is common with the fentanyl in that the remifentanil is a selective μ-opioid receptor agonist, but is different from the fentanyl in that the remifentanil is rapidly hydrolyzed by nonspecific esterase in blood and a living tissue and becomes the nonactive metabolite which is discharged from the kidney. The remifentanil is prompt in the appearance and disappearance of its analgesic action and does not have the property of accumulating in the body and further, is capable of easily controlling pain relief according to invasive stimulation. Because the remifentanil can be used for patients having a disorder in renal and liver functions without adjusting its capacity, the remifentanil is currently used in combination with an inhalation anesthetic and an intravenous anesthetic as an analgesic in introducing and maintaining general anesthesia (see nonpatent documents 1 and 2).

The remifentanil is soluble in water, but an aqueous solution thereof is unstable and cannot be stored for a long term. Therefore, currently lyophilized powder of the remifentanil is distributed and sold by accommodating it in containers such as a vial container.

A remifentanil injection solution to be used at an anesthetizing time is prepared by adding a large amount of water or an aqueous solution to a lyophilized remifentanil formulation. But when a large amount of water or the aqueous solution is directly added to the container accommodating the lyophilized remifentanil formulation, there occurs a danger that a remifentanil solution leaks from the container due to the rise of an internal pressure inside the container. Because the remifentanil is designated as a drug, it is necessary to perform a troublesome post-treatment when there occurs a trouble of the leak of the remifentanil solution from the container.

In consideration of the above-described problem, a method of preparing a remifentanil injection solution by performing complicated processes is proposed to administer the remifentanil injection solution to a patient at an anesthetizing time. The method includes the process of preparing a concentrate solution of the remifentanil by injecting a small amount of a dissolving solution (water, saline 5% glucose injection solution or the like) to a container such as a vial container accommodating a lyophilized remifentanil formulation to dissolve the remifentanil, the process of collecting the concentrate solution from the container, and the process of mixing a diluting solution (saline, 5% glucose injection solution or the like) with the concentrate solution to prepare a final remifentanil injection solution to be injected to the patient (see left-hand column of page 1655 of nonpatent document 1).

Normally, an anesthesiologist prepares the remifentanil injection solution by performing the above-described two-stage processes of dissolving the remifentanil in a small amount of the dissolving solution to prepare the concentrate solution and mixing the diluting solution with the concentrate solution to prepare the final remifentanil injection solution. Normally, the anesthesiologist performs the above-described complicated operation alone as a process for preparing the administration of the remifentanil injection solution. The preparation of the remifentanil injection solution required to be performed by carrying out the two-stage process may cause a risk of medication errors such as failure in adjusting the concentration of the remifentanil in the final injection solution.

In view of the above-described problems, there is a demand for the development of a remifentanil injection solution formulation which eliminates the need for performing the above-described complicated two-stage process and can be prepared by a simple operation of the anesthesiologist at a medical front, contains a correct amount of the remifentanil, and is excellent in its storage stability.

Of the opioid such as the sufentanil, an opioid high-concentration liquid medicine in which the opioid dissolves in an aromatic non-aqueous medium such as benzyl alcohol or benzyl benzoate at a high concentration of not less than 50 mg/mL is known. The opioid high-concentration liquid medicine is used to relieve pain (patent document 1). The opioid high-concentration liquid medicine of the patent document 1 is used to be continuously administered to a patient having a chronic pain for a long term, for example, several months or several years. To solve a conventional problem that the capacity of a medicine formulation is specifically limited (use of embedding pump or external pump) and that the concentration thereof is specifically limited (precipitation of medicine), the opioid high-concentration liquid medicine was developed as a 1.5 liquid medicine which can be provided without diluting the concentration thereof when a medicine having a high effective amount is needed.

To the contrary, the remifentanil injection solution is used to stabilize stress reactions of circulation dynamics caused by surgical invasion accompanied by the administration of an anesthesia and restrain sedative, analgesic, muscle relaxant actions, the rise of a blood pressure, and tachycardia caused by the surgical operation. The remifentanil injection solution is not used in combination with the inhalation anesthetic and the intravenous anesthetic. The remifentanil injection solution is different from the opioid high-concentration liquid medicine in this respect.

The aromatic non-aqueous medium such as the benzyl alcohol or the benzyl benzoate for use in the opioid such as the sufentanil and the like described in the patent document 1 has a disadvantage of being incapable of dissolving the remifentanil therein and accelerating the hydrolysis of the remifentanil. Thus, the aromatic non-aqueous medium cannot be used to prepare the remifentanil injection solution to be used at an anesthetizing time.

PRIOR ART DOCUMENTS

Patent Documents

Patent document 1: Patent No. 4969009

Nonpatent Document

Nonpatent document 1: "Anesthesia 21 century" vol. 9, No. 2-28, P. 1652-1665 (2007)
Nonpatent document 2: Medical Journal of Kagoshima City, vol. 46, No. 6, p. 12 (2007)

SUMMARY OF THE INVENTION

Problems to be Solved by the Invention

It is an object of the present invention to provide a remifentanil injection solution formulation excellent in its long-term storage stability.

More specifically, it is an object of the present invention to provide the remifentanil injection solution formulation which allows a remifentanil injection solution containing a correct amount of remifentanil to be easily prepared at one-step process by an anesthesiologist or the like at a medical front. That is, it is an object of the present invention to provide the remifentanil injection solution formulation to be produced without the need for performing a complicated two-step process of preparing a concentrate solution by dissolving a powder remifentanil formulation accommodated inside a container such as a vial container, collecting the concentrate solution from the container and mixing a diluting solution with the concentrate solution to prepare a final remifentanil injection solution.

Means for Solving the Problems

The present inventors have made researches to achieve the above-described object. As a result, they have found that by mixing the remifentanil and/or physiologically acceptable salts (in other words, pharmaceutically acceptable salts) thereof, water or ethanol and in addition a stabilizer with one another at a predetermined mixing ratio, the remifentanil and/or physiologically acceptable salts thereof dissolve well in the predetermined amount of the water or the ethanol and are stabilized by the stabilizer and that the resulting remifentanil and/or physiologically acceptable salts thereof hardly denatures, decomposes or precipitates and thus dissolve in the solution at a high survival rate, even after the solution is stored for a long term at a room temperature and are thus excellent in its long-term storage stability.

The present inventors have also found that in the remifentanil injection solution formulation, liquid polyhydric alcohol such as polyethylene glycol, propylene glycol, and the like are effective as the stabilizer and the polyethylene glycol is especially preferable as the stabilizer.

The present inventors have also found that in the remifentanil injection solution formulation, it is preferable to set the content ratio between the water and the stabilizer and the content ratio between the ethanol and the stabilizer to a specific range respectively to obtain the remifentanil injection solution formulation excellent in its long stability.

The present inventors have also found that by setting the content of the remifentanil and/or the physiologically acceptable salts thereof contained in the remifentanil injection solution formulation to a predetermined range, the remifentanil injection solution formulation can be effectively used at an anesthetizing site.

The present inventors have also found that by coloring the remifentanil injection solution formulation with a colorant, it is possible to prevent the occurrence of medical malpractice of erroneously injecting a diluting solution which does not contain the remifentanil and has not been mixed with the remifentanil injection solution formulation to a patient at the anesthetizing site. In this way, the present inventors have completed the present invention based on the above-described various findings they have obtained.

Mode for Carrying Out the Invention

The present invention is described in detail below.

The present invention includes (I) a remifentanil injection solution formulation (hereinafter referred to as "remifentanil injection solution formulation (I)") containing remifentanil (salts), water, and a stabilizer, and (H) remifentanil injection solution formulation (hereinafter referred to as "remifentanil injection solution formulation (II)") containing the remifentanil (salts), ethanol, and the stabilizer.

The remifentanil used in the remifentanil injection solution formulation (I) of the present invention and in the remifentanil injection solution formulation (II) thereof (both remifentanil injection solution formulations may be collectively referred to as "remifentanil injection solution formulation") are also known as methy4-(methoxycarbonyl)-4-[(1-oxopropyl)phenylamino]piperidine-1-propionic acid methyl ester.

In the present invention, as the remifentanil (salts), it is possible to use remifentanil itself not in the form of salts and one or not less than two kinds of salts selected from among physiologically acceptable remifentanil salts.

As the physiologically acceptable remifentanil salts, it is possible to exemplify hydrochloride, hydrobromate, sulfate, sulfonate, phosphate, tartrate, formate, acetate, propionate, benzoate, oxalate, succinate, citrate, glutamate, fumarate, aspartate, glutarate, stearate, butyrate, malonate, and lactate. In the present invention, it is possible to use one or not less than two kinds of the above-described remifentanil salts.

Of the above-described salts, the remifentanil and/or the remifentanil hydrochloride are favorably used as the remifentanil (salts) in the present invention. The remifentanil hydrochloride is more favorably used in terms of its availability.

As the "water" to be used for the remifentanil injection solution formulation (I) of the present invention, it is possible to use any water pharmaceutically, pharmacologically and physiologically acceptable. As the "water" to be used for the remifentanil injection solution formulation (I), it is possible to list distilled water, normal water, purified water, sterile purified water, water for injection, and distilled water for injection. The definition of these kinds of water is based on Japanese Pharmacopoeia 16th edition.

The remifentanil injection solution formulation (I) contains the water at a rate of 0.007 to 0.025 mL per 1 mg of the remifentanil. It is favorable for the remifentanil injection solution formulation (I) to contain the water at a rate of favorably 0.007 to 0.02 mL, more favorable to contain it at a rate of 0.008 to 0.015 mL, and especially favorable to contain it at a rate of 0.009 to 0.015 mL per 1 mg of the remifentanil.

In the present specification, "per 1 mg of the remifentanil" means "per 1 mg of the remifentanil not in the form of salts".

In a case where the remifentanil injection solution formulation (I) contains not less than two kinds of the remifentanil (salts), the above-described content rate of the water means its content rate per the total amount of 1 mg of the remifentanil.

By setting the content of the water per 1 mg of the remifentanil to the above-described range, the remifentanil (salts) dissolves preferably in the water and is stabilized as it is by the stabilizer. Thus, even after the remifentanil injection solution formulation (I) is stored at the room temperature for a long term, the remifentanil is restrained from denaturing, decomposing, and precipitating and thus dissolves and is maintained as it is in the solution at a high survival rate. Therefore, the remifentanil injection solution formulation (I) is excellent in its long-term storage stability.

In a case where the content rate of the water per 1 mg of the remifentanil is less than 0.007 mL, the remifentanil (salts) does not sufficiently dissolve in the water and is liable to precipitate during the storage of the remifentanil injection solution formulation (I), even in a case where the remifentanil (salts) has dissolved therein. On the other hand, in a case where the content rate of the water per 1 mg of the remifentanil is not less than 0.007 ML, favorably not less than 0.008 mL, and more favorably not less than 0.009 mL, it is possible to reliably restrain the remifentanil (salts) from precipitating, even when the remifentanil injection solution formulation is placed in adverse conditions for the stability thereof.

On the other hand, in a case where the content rate of the water per 1 mg of the remifentanil exceeds 0.025 mL, there is no problem in terms of the solubility of the remifentanil (salts). But even though the remifentanil injection solution formulation contains the stabilizer, the remifentanil (salts) denatures and decomposes and thus its survival rate decreases below 90% in a case where the remifentanil injection solution formulation is stored for a long term not less than one year at the room temperature, as understood from the result of a severe test in which the remifentanil injection solution formulation was stored for one week at 60 degrees C. (corresponding to storage for one year at room temperature). In a case where the content rate of the water per 1 mg of the remifentanil is not more than 0.02 mL, as understood from the result of a severe test in which the remifentanil injection solution formulation was stored for three weeks at 60 degrees C. (corresponding to storage for three years at room temperature), its survival rate can be maintained at a high level of not less than 90% even when the remifentanil injection solution formulation is stored for a long time not less than three years at the room temperature.

In the present specification, the content rate (mL) of the water per 1 mg of the remifentanil in the remifentanil injection solution formulation (I) means the content rate (mL) of the water at 20 degrees C.

The remifentanil injection solution formulation (II) contains the ethanol at a rate of 0.10 to 0.50 mL per 1 mg of the remifentanil. It is favorable for the remifentanil injection solution formulation (II) to contain the ethanol at a rate of 0.10 to 0.35 mL of ethanol and more favorable to contain the ethanol at a rate of 0.12 to 0.30 mL per 1 mg of the remifentanil.

In a case where the remifentanil injection solution formulation (II) contains not less than two kinds of the remifentanil (salts), the above-described content rate of the ethanol means its content rate per the total amount of 1 mg of the remifentanil.

By setting the content of the ethanol per 1 mg of the remifentanil to the above-described range, the remifentanil (salts) dissolves well in the ethanol and is stabilized by the stabilizer contained in the remifentanil injection solution formulation (II). Thereby even after the remifentanil injection solution formulation (II) is stored for a long term at the room temperature, the remifentanil hardly denatures and decomposes and is maintained in the solution at a high survival rate and is thus excellent in its long-term storage stability.

In a case where the content rate of the ethanol per 1 mg of the remifentanil is below 0.10 mL, the remifentanil (salts) does not sufficiently dissolve in the ethanol and is liable to precipitate during the storage of the remifentanil injection solution formulation (II) even in a case where the remifentanil (salts) has dissolved therein. On the other hand, in a case where the content rate of the ethanol per 1 mg of the remifentanil is not less than 0.10 mL, favorably not less than 0.12 mL, and most favorably not less than 0.15 mL, it is possible to reliably restrain the remifentanil (salts) from precipitating even when the remifentanil injection solution formulation is placed in adverse conditions for the stability thereof.

On the other hand, in a case where the content rate of the ethanol per 1 mg of the remifentanil exceeds 0.50 mL, there is no problem in terms of the solubility of the remifentanil (salts). But even though the remifentanil injection solution formulation (II) contains the stabilizer, the remifentanil (salts) denatures and decomposes and thus its survival rate decreases below 90% in a case where the remifentanil is stored for a long term not less than one year at the room temperature, as understood from the result of a severe test in which the remifentanil was stored for one week at 60 degrees C. (corresponding to storage for one year at room temperature). In a case where the content rate of the ethanol per 1 mg of the remifentanil is not more than 0.3 mL, as understood from the result of a severe test in which the remifentanil injection solution formulation (II) was stored for three weeks at 60 degrees C. (corresponding to storage for three years at room temperature), the survival rate of the remifentanil can be maintained at a high level of not less than 90% even when the remifentanil injection solution formulation (II) is stored for a long term not less than three years at the room temperature.

In the present specification, the content rate (mL) of the ethanol per 1 mg of the remifentanil in the remifentanil injection solution formulation (II) means the content rate (mL) of the ethanol at 20 degrees C.

The stabilizer to be used in the remifentanil injection solution formulation of the present invention is used to dissolve the remifentanil (salts) stably in the water or in the ethanol. The stabilizer which can be preferably used is liquid polyhydric alcohol physiologically acceptable. As concrete examples of the stabilizer, it is possible to exemplify liquid polyethylene glycol, liquid propylene glycol, and the like.

Of the stabilizers, the liquid polyethylene glycol having a molecular weight of 200 to 600 daltons is more favorably used. As an example of the liquid polyethylene glycol having the molecular weight in the range of 200 to 600 daltons, macrogol 400, macrogol 200, and the like are exemplified.

In the remifentanil injection solution formulation (I) of the present invention, the content ratio between the water and the stabilizer is set to favorably 2:23 to 2:198, more favorably 2:23 to 2:98, and most favorably 2:48 to 2:98 in a volume ratio.

In the remifentanil injection solution formulation (II) of the present invention, the content ratio between the ethanol and the stabilizer is set to preferably 3:2 to 3:7 in a volume ratio.

By setting the volume ratio between the water and the stabilizer in the remifentanil injection solution formulation (I) and the volume ratio between the ethanol and the stabilizer in the remifentanil injection solution formulation (II) to the above-described range respectively, the amount of the stabilizer in the remifentanil injection solution formulation (f) and that of the stabilizer in the remifentanil injection solution formulation (II) are sufficient. Thus, the water or the ethanol is restrained from transpiring during the storage of the remifentanil injection solution formulation. Thereby the long-term storage stability of the remifentanil injection solution formulation can be secured.

In the present specification, the content ratio (volume ratio) between the water and the stabilizer in the remifentanil injection solution formulation (I) means the content ratio (volume ratio) therebetween at 20 degrees C. the content ratio (volume ratio) between the ethanol and the stabilizer in the remifentanil injection solution formulation (H) means the content ratio (volume ratio) therebetween at 20 degrees C.

In a case where the content ratio between the water and the stabilizer in the remifentanil injection solution formulation (I) departs from the above-described range and the content ratio of the stabilizer is too low, it is difficult to obtain the remifentanil injection solution formulation in which the remifentanil (salts) has stably dissolved in the water. On the other hand, in a case where the content ratio of the stabilizer in the remifentanil injection solution formulation (II) is too high, an osmotic pressure is liable to become high.

In a case where the content ratio between the ethanol and the stabilizer in the remifentanil injection solution formulation (II) departs from the above-described range and the content ratio of the stabilizer is too low, it is difficult to obtain the remifentanil injection solution formulation in which the remifentanil (salts) has stably dissolved in the ethanol. On the other hand, in a case where the content ratio of the stabilizer in the remifentanil injection solution formulation (II) is too high, an osmotic pressure is liable to become high.

It is favorable for the remifentanil injection solution formulation [the remifentanil injection solution formulation (I) and the remifentanil injection solution formulation (II)] of the present invention to contain 1 to 1.0 mg of the remifentanil (salts) not in the form of salts and more favorably to contain 2 to 5 mg thereof per 1 mL of the remifentanil injection solution formulation.

In a case where the content of the remifentanil (salts) per of the remifentanil injection solution formulation is a predetermined amount (for example, 1 mg, 2 mg or 5 mg) falling within the above-described range, it is possible to easily prepare the remifentanil injection solution, having a predetermined concentration of the remifentanil, which can be used as it is at an anesthetizing time by taking out a whole amount of the remifentanil injection solution formulation from containers such as a vial, an ample or a prefilled syringe and mixing the remifentanil injection solution formulation with a predetermined amount of a diluting solution.

Because the remifentanil (salts) is a drug, it is necessary to keep it in a safe. The diluting solution for the remifentanil injection solution having a lower concentration (namely, diluting solution for remifentanil injection solution in which content of remifentanil (salts) contained in remifentanil injection solution is smaller than the above-described range) necessitates a wide space (large safe or a plurality of safes) for storing a predetermined amount of the remifentanil injection solution formulation to be provided, which is uneconomical for medical institutions. From this standpoint, it is desirable to set the content of the remifentanil (salts) contained in the remifentanil injection solution formulation to the above-described range.

The remifentanil injection solution formulation of the present invention may or may not contain a colorant. A remifentanil injection solution (final injection solution), to be used at an anesthetizing time, which is obtained by mixing a diluting solution with the remifentanil injection solution formulation of the present invention containing the colorant is colored.

It is possible to visually confirm that the remifentanil (salts) is contained in the colored final remifentanil injection solution. Thus, the colored remifentanil injection solution can be distinguished from a colorless diluting solution. Thereby it is possible to prevent the occurrence of medical malpractice of erroneously injecting the diluting solution not containing the remifentanil injection solution formulation to a patient.

As colorants to be used to color the remifentanil injection solution formulation of the present invention therewith, it is possible to exemplify cyanocobalamin, indocyanine green, and indigocarmine.

Any of these colorants contained in the remifentanil injection solution formulation does not decompose or deteriorate the remifentanil (salts), i.e., does not deteriorate the quality of the remifentanil or the anesthesia and analgesic functions and storage stability of the remifentanil injection solution formulation.

Of the above-described colorants, the cyanocobalamin is more favorably used. The reason is as follows:
When the cyanocobalamin is contained in the liquid remifentanil injection solution formulation, the liquid remifentanil injection solution formulation does not fades in its color or discolor even after it is stored for a long term and is capable of maintaining its initial color tone.

The remifentanil injection solution for anesthesia prepared by diluting the remifentanil injection solution formulation containing the cyanocobalamin with the diluting solution does not absorb light having a wavelength of 660 nm used as a measuring wavelength in a pulse oximeter. Therefore, even though the remifentanil injection solution for anesthesia contains the cyanocobalamin, the pulse oximeter operates normally.

On the other hand, in a case where the indocyanine green or the indigocarmine are contained the liquid remifentanil injection solution formulation, the liquid remifentanil injection solution formulation fade in the color thereof or discolor during the storage of the liquid remifentanil injection solution formulation and are thus incapable of maintaining the initial color thereof.

In a case where the colorant is contained in the remifentanil injection solution formulation, it is preferable to use 0.02 to 1.5 mg of the colorant per 1 mg of the remifentanil, although the content of the colorant is different according to the kind thereof.

The remifentanil injection solution formulation (I) of the present invention may contain only the remifentanil (salts), the water, and the stabilizer or may contain only the remifentanil (salts), the water, the stabilizer, and the colorant. Further, the remifentanil injection solution formulation (I) of the present invention may further contain ethanol in an amount not departing from the gist of the present invention.

The remifentanil injection solution formulation (II) of the present invention may contain only the remifentanil (salts), the ethanol, and the stabilizer or may contain only the remifentanil (salts), the ethanol, the stabilizer, and the colorant. Further, the remifentanil injection solution formulation (II) of the present invention may contain the water in an amount not departing from the gist of the present invention.

The remifentanil injection solution formulation (I) of the present invention and the remifentanil injection solution formulation (II) thereof may contain other components (for example, glycine) as necessary in a range in which the use of the other components does not deteriorate the dissolution stability and storage stability of the remifentanil injection solution formulation.

The remifentanil injection solution formulation of the present invention can be stored, distributed, and sold by accommodating it inside a vial, an ample, a syringe, and the like. The material of the container is not specifically limited, but may be formed of any of glass, organic polymer such as plastic, rubber (elastomer), and composites of these materials. In a case where the container formed of the organic polymer is used, the container can be formed of the organic polymer such as polypropylene, cyclic olefin polymer, the rubber (elastomer), and the like.

The size of the container accommodating the remifentanil injection solution formulation is not specifically limited, but can be set to an appropriate size. For example, it is possible to set the size of the container to 02 to 20 mL.

The capacity of the remifentanil injection solution formulation to be accommodated inside the container is not specifically limited, but an appropriate amount thereof can be accommodated therein. The remifentanil injection solution formulation may be accommodated inside each container in such a way that the amount of the remifentanil to be contained in one container is 1 to 10 mg and favorably 2 mg or 5 mg.

It is possible to provide the remifentanil injection solution formulation of the present invention in the form of a kit formulation prepared by combining a container accommodating the remifentanil injection solution formulation and a container accommodating the diluting solution with each other. As the diluting solution to be used for the kit formulation, it is possible to use saline, 5% glucose injection solution, and the like.

The use of the kit formulation does not necessitate a medical worker such as an anesthetist to take time and labor required to separately prepare or procure the diluting solution in addition to the remifentanil injection solution formulation. It is possible to easily prepare a remifentanil injection solution for anesthesia by only diluting the remifentanil injection solution formulation of the kit formulation with the diluting solution thereof.

The method for producing the remifentanil injection solution formulation of the present invention is not specifically limited. It is possible to adopt any method capable of producing the remifentanil injection solution formulation (I) containing the remifentanil (salts), the water, and the stabilizer uniformly mixed with one another, the remifentanil injection solution formulation (II) containing the remifentanil (salts), the ethanol, and the stabilizer uniformly mixed with one another or the remifentanil injection solution formulation containing the remifentanil (salts), the water or the ethanol, the stabilizer uniformly and the colorant mixed with one another.

Although the method for producing the remifentanil injection solution formulation of the present invention is not specifically limited, it is possible to obtain the remifentanil injection solution formulation of the present invention by mixing the remifentanil (salts), the water, the stabilizer the colorant, and other components with one another at 10 to 80 degrees C. and favorably 20 to 50 degrees C. or mixing the remifentanil (salts), the ethanol, the stabilizer, the colorant, and other components with one another at 10 to 80 degrees C. and favorably 20 to 50 degrees C. to form a solution in which the remifentanil has uniformly dissolved in the water or the ethanol, aseptically filtering the solution, filling a predetermined amount of the solution in a container, and subjecting the solution to high-pressure steam sterilization. The aseptic filtration and the high-pressure steam sterilization can be performed by using methods similar to those conventionally adopted in producing the injection solution formulation.

It is possible to easily obtain the final remifentanil injection solution, to be used at an anesthetizing time, which correctly contains a predetermined concentration of the remifentanil (salts) by taking out a whole amount or a predetermined amount of the remifentanil injection solution formulation of the present invention from a container by using an appropriate means (for example, syringe, dropper, container connectable with syringe) and mixing the remifentanil injection solution formulation with a predetermined amount of the diluting solution (for example, saline, 5% glucose solution) to dilute the remifentanil injection solution formulation therewith.

EXAMPLES

The present invention is specifically described below by using examples. But the present invention is not limited by the following examples.

Example 1

(1) 2.20 mg of remifentanil hydrochloride (remifentanil: 2.00 mg), 1.10 g (0.98 mL; specific gravity: 1.12 g/mL) of macrogol 400 (polyethylene glycol 400, stabilizer), and 0.02 mL of water were mixed with one another at 20 degrees C. to prepare a remifentanil solution (concentration of remifentanil=2 mg/mL) containing 2 mg of the remifentanil per 1 mL of the solution.
(2) After the remifentanil solution obtained in the above (I) was aseptically filtered, 1 mL of the remifentanil solution was filled in each container (syringe in which gasket was made of butyl rubber, and syringe body was made of cyclic polyolefin) having a capacity of 1 mL. Thereafter the containers were subjected to high-pressure steam sterilization. In this manner, formulations for prefilled syringes (remifentanil injection solution formulation) in each of which a remifentanil injection solution was filled were produced.

Example 2

(1) 2.20 mg of the remifentanil hydrochloride remifentanil: 2.00 mg), 1.08 g (0.96 mL) of the macrogol 400 (stabilizer), and 0.04 mL of water were mixed with one another at 20 degrees C. to prepare a remifentanil solution (concentration of remifentanil=2 mg/mL) containing 2 mg of the remifentanil per in L of the solution.

(2) After the remifentanil solution obtained in the above (1) was aseptically filtered, 1 mL of the remifentanil solution was filled in each container, having the capacity of which was the same as that used in the example 1. Thereafter the containers were subjected to high-pressure steam sterilization. In this manner, formulations for prefilled syringes (remifentanil injection solution formulation) in each of which a remifentanil injection solution was filled were produced.

Example 3

(1) 2.20 mg of the remifentanil hydrochloride remifentanil: 2.00 mg), 1.06 g (0.95 mL) of the macrogol 400 (stabilizer), and 0.05 mL of water were mixed with one another at 20 degrees C. to prepare a remifentanil solution (concentration of remifentanil 2 mg/ML) containing 2 mg of the remifentanil per 1 mL of the solution.

(2) After the remifentanil solution obtained in the above (1) was aseptically filtered, 1 mL of the remifentanil solution was filled in each container, having the capacity of 1 mL, which was the same as that used in the example 1. Thereafter the containers were subjected to high-pressure steam sterilization. In this manner, formulations for prefilled syringes (remifentanil injection solution formulation) in each of which a remifentanil injection solution was filled were produced.

Comparison Example 1

(1) 2.20 mg of the remifentanil hydrochloride (remifentanil: 2.00 mg), 1.01 g (0.90 mL) of the macrogol 400 (stabilizer), and 0.10 mL of water were mixed with one another at 20 degrees C. to prepare a remifentanil solution (concentration of remifentanil=2 mg/mL) containing 2 mg of the remifentanil per 1 mL of the solution.

(2) After the remifentanil solution obtained in the above (1) was aseptically filtered, of the remifentanil solution was filled in each container, having the capacity of 1 mL, which was the same as that used in the example 1. Thereafter the containers were subjected to high-pressure steam sterilization. In this manner, formulations for prefilled syringes (remifentanil injection solution formulation) in each of which a remifentanil injection solution was filled were produced.

Comparison Example 2

(1) 2.20 mg of the remifentanil hydrochloride (remifentanil: 2.00 mg), 1.11 g (0.99 mL) of the macrogol 400 (stabilizer), and 0.01 mL of water were mixed with one another at 20 degrees C. with the intention of preparing a remifentanil solution (concentration of remifentanil=2 mg/mL) containing 2 mg of the remifentanil per 1 mL of the solution. But the remifentanil salt did not completely dissolve, and a part of the remifentanil salt remained in a solid state in the solution. Thus, the remifentanil injection solution formulation could not be prepared.

[Stability Test]

The remifentanil injection solution formulation obtained in each of the above-described examples 1 through 3 and the comparison example 1 was stored at 60 degrees C. for one week and three weeks. The amount of the remifentanil in each solution was determined when the test started, when one week passed after the test finished, and when three weeks passed after the test finished. The survival rate (%) of the remifentanil when one week passed and that of the remifentanil when three weeks passed were determined with respect to the survival rate set to 100% when the test started. In each example and comparison example, the survival rate of the remifentanil was determined by using three specimens, conducting the same test, and taking the average of three values.

The results are shown in table 1.

[Quantitative Method]

(1) After 1 mL of the remifentanil injection solution formulation obtained in each of the examples 1, through 3 and the comparison example 1 was correctly measured, water was added to each remifentanil injection solution formulation to obtain solutions having a volume of 10 mL. After 4 mL of each of these solutions was correctly measured, 8 mL of an internal standard solution [mobile phase solution (1→40000) of methyl parahydroxybenzoate] was added to each of the solutions having the volume of 4 mL. Thereafter a mobile phase [mixed solution of phosphoric acid-based buffer solution (pH 2.5):acetonitrile=78:22 (volume ratio)] was further added to each of the solutions to obtain specimen solutions each having a volume of 20 mL.

(2) Separately from the above-described (1), after about 20 mg of remifentanil hydrochloride was precisely measured, the mobile phase [mixed solution of phosphoric acid-based buffer solution (pH 2.5):acetonitrile=78:22 (volume ratio)] was added to solutions of the remifentanil hydrochloride to obtain solutions each having a volume of exactly 100 mL. After 4 mL of each of these solutions was correctly measured, of the internal standard solution was correctly added to each of these solutions. Thereafter the mobile phase [mixed solution of phosphoric acid based buffer solution (pH 2.5):acetonitrile=78:22 (volume ratio)] was added to the solutions to obtain specimen solutions each having a volume of 20 mL.

(3) By using 10 μL of each of the specimen solutions prepared in the above-described (1) and 10 μL of each of the specimen solutions prepared in the above-described (2), the amount of each remifentanil was measured by using a chromatographic method in conditions described below.

The peak area of each solution was measured by an automatic integration method to determine the amount of each remifentanil from the ratio of the peak area of the remifentanil to the peak area of the internal standard solution [mobile phase solution (1→40000) of methyl parahydroxybenzoate)].

[Measuring Condition]

Detector: ultraviolet absorption meter (measured wavelength: 210 nm)

Column: a stainless steel pipe having an inner diameter of 4.6 mm and a length of 25 cm in which 5 μm of octadecylsilyl silica gel for use in a liquid chromatograph was filled.

Temperature of column: constant in the vicinity of 40 degrees C.

Mobile phase: obtained by dissolving 2.9 g of ammonium dihydrogen phosphate in 1000 mL of water and adding phosphoric acid to the obtained solution to adjust the pH thereof to about 2.5 and adding 220 mL of acetonitrile to 780 mL of the solution.

Internal standard solution: mobile phase solution of methyl parahydroxybenzoate (1 to 40000)

Flow rate: The holding period of time of the peak of the remifentanil was set about 10 minutes.

TABLE 1

|  | Example 1 | Example 2 | Example 3 | Comparison example 1 | Comparison example 2 |
|---|---|---|---|---|---|
| Remifentanil contained in remifentanil injection solution formulation | 2.00 mg | 2.00 mg | 2.00 mg | 2.00 mg | 2.00 mg |
| Water (amount of water per 1 mg of remifentanil) | 0.02 mL (0.01 mL) | 0.04 mL (0.02 mL) | 0.05 mL (0.025 mL) | 0.10 mL (0.05 mL) | 0.01 mL (0.005 mL) |
| Stabilizer (macrogol 400) | 1.10 g (0.98 mL) | 1.08 g (0.96 mL) | 1.06 g (0.95 mL) | 1.01 g (0.90 mL) | 1.11 g (0.99 mL) |
| Water/stabilizer (volume ratio) | 2/98 | 4/96 | 5/95 | 10/90 | 1/99 |
| Total amount of remifentanil injection solution formulation (mL) | 1.00 mL | 1.00 mL | 1.00 mL | 1.00 mL | 1.00 mL |
| Survival rate of remifentanil after storage of 1 week at 60 degrees C. | 99.8% | 96.5% | 95.4% | 83.8% | —[1] |
| Survival rate of remifentanil after storage of 3 weeks at 60 degrees C. | 96.5% | 90.0% | 86.5% | 70.1% | —[1] |

—[1] A part of the remifentanil salt remained in a solid state in the solution and thus, the remifentanil injection solution formulation could not be prepared.

As shown in the table 1, the remifentanil injection solution formulation of each of the examples 1 through 3 contained the water in the range of 0.007 to 0.025 mL per 1 mg of the remifentanil and the stabilizer. Therefore, the remifentanil (salts) contained in the remifentanil injection solution formulation of each of the examples 1 through 3 did not precipitate but dissolved well therein and was in a liquid state. Further in the remifentanil injection solution formulation of each of the examples 1 through 3, the survival rate of the remifentanil was as high as not less than 95% after the rernifentanil injection solution formulation was stored at 60 degrees C. for one week (corresponding to storage for one year at room temperature), which indicates that the remifentanil injection solution formulation of each of the examples 1 through 3 was excellent in the long-term storage stability thereof. In the remifentanil injection solution formulation of each of the examples 1 and 2 containing the water in the range of 0.01 to 0.02 mL per 1 mg of the remifentanil and the stabilizer, the survival rate of the remifentanil was as high as not less than 90% after the remifentanil injection solution formulations were stored at 60 degrees C. for three weeks (corresponding to storage for three years at room temperature), which indicates that the remifentanil injection solution formulation of each of the examples 1 and 2 was excellent in the long-term storage stability thereof.

On the other hand, the remifentanil injection solution formulation of the comparison example 1 contained the water in the amount exceeding 0.025 mL which is the upper limit set in the present invention per 1 mg of the remifentanil. Thus, after the remifentanil injection solution formulation was stored at 60 degrees C. for one week, the survival rate of the remifentanil was as low as less than 85%, which indicates that the remifentanil injection solution formulation of the comparison example 1 was inferior in its long-term storage stability.

The remifentanil injection solution formulation of the comparison example 2 contained the water in the amount lower than 0.07 mL which is the lower limit set in the present invention per 1 mg of the remifentanil. Thus, the remifentanil (salts) did not completely dissolve in the solution and partly precipitated, which made it impossible to produce the remifentanil injection solution formulation.

Example 4

2.20 mg of the remifentanil hydrochloride (remifentanil: 2.00 mg), 0.78 g (0.70 mL) of the macrogol 400 (stabilizer), and 0.24 g of anhydrous ethanol (0.30 mL, specific gravity: 0.79) were mixed with one another at 20 degrees C. to prepare a remifentanil solution (concentration of remifentanil=2 mg/mL) containing 2 mg of the remifentanil per 1 mL of the solution.

(2) After the remifentanil solution obtained in the above (1) was aseptically filtered, 1 mL, of the remifentanil solution was filled in each container, having the capacity of 1 mL, which was the same as that used in the example 1. Thereafter the containers were subjected to high-pressure steam sterilization. In this manner, formulations for pre-filled syringes (remifentanil injection solution formulation) in each of which a remifentanil injection solution was filled were produced.

Example 5

2.20 mg of the remifentanil hydrochloride remifentanil: 2.00 mg), 0.45 g (0.40 mL) of the macrogol 400 (stabilizer), and 0.47 g of the anhydrous ethanol (0.60 mL, specific gravity: 0.79) were mixed with one another at 20 degrees C. to prepare a remifentanil solution (concentration of remifentanil=2 mg/mL) containing 2 mg of the remifentanil per 1 mL of the solution.

(2) After the remifentanil solution obtained in the above (1) was aseptically filtered, 1 mL of the remifentanil solution was filled in each container, having the capacity of 1 mL, which was the same as that used in the example 1. Thereafter the containers were subjected to high-pressure steam sterilization. In this manner, formulations for pre-filled syringes (remifentanil injection solution formulation) in each of which a remifentanil injection solution was filled were produced.

Comparison Example 3

2.20 mg of the remifentanil hydrochloride (remifentanil: 2.00 mg) and 0.79 g of the anhydrous ethanol (1.00 mL, specific gravity: 0.79) were mixed with one another at 20 degrees C. to prepare a remifentanil solution (concentration of remifentanil=2 mg/mL) containing 2 mg of the remifentanil per 1 mL, of the solution.

(2) After the remifentanil solution obtained in the above (1) was aseptically filtered, 1 mL of the remifentanil solution was filled in each container, having the capacity of 1 mL, which was the same as that used in the example 1. Thereafter the containers were subjected to high-pressure steam sterilization. In this manner, formulations for pre-filled syringes (remifentanil injection solution formulation) in each of which a remifentanil injection solution was filled were produced.

Comparison Example 4

2.20 mg of the remifentanil hydrochloride remifentanil: 2.00 mg), 0.94 g (0.84 mL) of the macrogol 400 (stabilizer), and 0.13 g of the anhydrous ethanol (0.16 mL, specific gravity: 0.79) were mixed with one another at 20 degrees C. with the intention of preparing a remifentanil solution (concentration of remifentanil=2 mg/mL) containing 2 mg of the remifentanil per 1 mL, of the solution. But the remifentanil salt did not completely dissolve, and a part of the remifentanil salt remained in a solid state in the solution. Thus, the remifentanil injection solution formulation could not be prepared.

[Stability Test 2]

The remifentanil injection solution formulation obtained in each of the above-described examples 4 and 5 and the comparison example 3 were stored at 60 degrees C. for one week and three weeks. By carrying out a method same as that adopted in the example 1, the amount of each remifentanil in the solution was determined when the test started, when one week passed after the test finished, and when three weeks passed after the test finished. The survival rate (%) of the remifentanil when one week and three weeks passed after the test finished was determined with respect to the survival rate thereof set to 100% when the test started. In each of the examples and comparison example, the survival rate of the remifentanil was determined by using three specimens, conducting the same test, and taking the average of three values.

The results are shown in table 2.

TABLE 2

|  | Example 4 | Example 5 | Comparison example 3 | Comparison example 4 |
|---|---|---|---|---|
| Remifentanil contained in remifentanil injection solution formulation | 2.00 mg | 2.00 mg | 2.00 mg | 2.00 mg |
| Anhydrous ethanol (amount of anhydrous ethanol) per 1 mg of remifentanil) | 0.30 mL (0.15 mL) | 0.60 mL (0.30 mL) | 1.00 mL (0.50 mL) | 0.16 mL (0.08 mL) |
| Stabilizer (macrogol 400) | 0.78 (0.70 mL) | 0.45 g (0.40 mL) | — | 0.94 g (0.84 mL) |
| Anhydrous ethanol/stabilizer (volume ratio) | 30/70 | 60/40 | 100/0 | 16/84 |
| Total amount of remifentanil injection solution formulation (mL) | 1.00 mL | 1.00 mL | 1.00 mL | 1.00 mL |
| Survival rate of remifentanil after storage of 1 week at 60 degrees C. | 99.0% | 96.4% | 89.6% | —[1] |
| Surival rate of remifentanil after storage of 3 weeks at 60 degrees C. | 93.1% | 90.0% | 85.6% | —[1] |

[1] A part of the remifentanil salt remained in a solid state in the solution and thus, the remifentanil injection solution formulation could not be prepared.

As shown in the table 2, the remifentanil injection solution formulation of each of the examples 4 and 5 contained the ethanol in the range of 0.10 to 0.50 mL per 1 mg of the remifentanil and the stabilizer. Therefore, the remifentanil (salts) contained in the remifentanil injection solution formulation of each of the examples 4 and 5 did not precipitate, but dissolved well therein and was in a liquid state. Further in the remifentanil injection solution formulation of each of the examples 4 and 5, the survival rate of the remifentanil was as high as not less than 96% after the remifentanil injection solution formulation was stored at 60 degrees C. for one week (corresponding to storage for one year at room temperature), which indicates that the remifentanil injection solution formulation of each of the examples 4 and 5 was excellent in its long-term storage stability. The remifentanil injection solution formulation of each of the examples 4 and 5 contained the ethanol in the range of 0.10 to 0.50 mL per 1 mg of the remifentanil and the stabilizer. Thereby the survival rate of the remifentanil contained in the remifentanil injection solution formulation each of the examples 4 and 5 was as high as 90% after the remifentanil injection solution formulation was stored at 60 degrees C. for three weeks (corresponding to storage for three years at room temperature), which indicates that the remifentanil injection solution formulation of each of the examples 4 and 5 was excellent in the long-term storage stability thereof.

On the other hand, the remifentanil injection solution formulation of the comparison example 3 contained the ethanol in the range of 0.10 to 0.50 mL, but did not contain the stabilizer. Thus, after the remifentanil injection solution formulation was stored at 60 degrees C. for one week (corresponding to storage for one year at room temperature), the survival rate of the remifentanil was as low as less than 90%. After the remifentanil injection solution formulation was stored at 60 degrees C. for three weeks (corresponding to storage for three years at room temperature), the survival rate of the remifentanil was as low as less than 85% level.

The remifentanil injection solution formulation of the comparison example 4 contained the ethanol in the amount less than 0.10 mL which is the lower limit set in the present invention per 1 mg of the remifentanil. Thus, the remifentanil (salts) did not completely dissolve in the solution and partly precipitated, which made it impossible to produce the remifentanil injection solution formulation.

Example 6

(1) 2.20 mg of the remifentanil hydrochloride (remifentanil: 2.00 mg), 1.02 g (0.98 mL, specific gravity: 1.04 g/mL) of propylene glycol (stabilizer), and 0.02 mL of water were mixed with one another at 20 degrees C. to prepare a remifentanil solution (concentration of remifentanil=2 mg/mL) containing 2 mg of the remifentanil per 1 mL of the solution.

(2) After the remifentanil solution obtained in the above (1) was aseptically filtered, 1 mL of the remifentanil solution was filled in each container, having the capacity of 1 mL, which was the same as that used in the example 1. Thereafter the containers were subjected to high-pressure steam sterilization. In this manner, formulations for pre-filled syringes (remifentanil injection solution formulation) in each of which a remifentanil injection solution was filled were produced.

(3) After the remifentanil injection solution formulation obtained in the above-described (2) was stored at 60 degrees C. for one week, the amount of the remifentanil contained in the solution was determined when the test started and when one week passed after the test started by carrying out the same method as that adopted in the example 1. In this way, the survival rate (%) of the remifentanil when one week passed after the test started was determined with respect to the survival rate of the remifentanil set to 100% when the test started. As a result, the survival rate of the remifentanil after the remifentanil injection solution formulation was stored at 60 degrees C. for one week (corresponding to storage at room temperature for one year) was 93.5%.

Example 7

Except that 0.2 mg of cyanocobalamin was added as a colorant to the solution of the remifentanil prepared in (1) of the example 1, the same operation as that performed in (1) and (2) of the example 1 was performed to produce the remifentanil injection solution formulation colored in red.

After the remifentanil injection solution formulation obtained in the above-described manner was stored at 60 degrees C. for three weeks, the survival rate of the remifentanil in the injection solution formulation was measured by carrying out the above-described method. As a result, the survival rate of the remifentanil was as high as not less than 95%. In addition, after the remifentanil injection solution formulation was stored at 60 degrees C. for three weeks, the remifentanil injection solution formulation did not fade in its color or discolor and maintained its initial good color tone.

INDUSTRIAL APPLICABILITY

Although the remifentanil injection solution formulation of the present invention is a liquid medicine, the remifentanil contained therein hardly denatures or decompose and is thus maintained in the solution at a high survival rate even after the remifentanil injection solution formulation is stored for a long term at the room temperature. Thus, the remifentanil injection solution formulation is excellent in its long-term storage stability.

By using the remifentanil injection solution formulation of the present invention, a medical worker who performs anesthesia at a medical front is capable of easily preparing the final remifentanil injection solution to be used at an anesthetizing time by merely mixing the diluting solution with a predetermined amount of the remifentanil injection solution formulation of the present invention. Thus, it is unnecessary to perform the conventional complicated two-stage process of dissolving the powdery remifentanil (salts) with a small amount of the dissolving solution and thereafter diluting it with the diluting solution to prepare the final remifentanil injection solution to be used at the anesthetizing times. Therefore, the remifentanil injection solution formulation of the present invention is very useful as an analgesic at the anesthetizing time.

Effect of the Invention

Although the remifentanil injection solution formulation of the present invention is a liquid medicine, it is excellent in its long-term storage stability. Even after the remifentanil injection solution formulation is stored for a long term at the room temperature, the remifentanil hardly denatures or decompose and is thus maintained in the solution at a high survival rate.

In the remifentanil injection solution formulation of the present invention, the remifentanil and/or the physiologically acceptable salts thereof [hereinafter may be referred to as "remifentanil (salts)] are dissolved in water or ethanol and takes the form of a liquid state. Therefore, at a medical front where anesthesia is performed, by merely mixing a predetermined amount of the diluting solution with the remifentanil injection solution formulation of the present invention, it is possible to easily prepare the final remifentanil injection solution to be used at an anesthetizing time. Thus, it is unnecessary to perform the conventional complicated two-step process of preparing the concentrate solution by dissolving the powdery remifentanil (salts) with a small amount of the dissolving solution and thereafter collecting the concentrate solution and diluting it with the diluting solution to finally prepare the remifentanil injection solution to be used at the anesthetizing time.

At the medical front where anesthesia is performed, health care workers including a doctor only performs a one-step preparing process of mixing a predetermined amount of the diluting solution with the remifentanil injection solution formulation of the present invention. Therefore, it is possible to easily prepare the final remifentanil injection solution which contains a correct amount of the remifentanil and is used at an anesthetizing time without making a mistake in adjusting the concentration of the remifentanil.

It is possible to clearly distinguish the remifentanil injection solution formulation of the present invention containing the colorant in addition to the above-described components and the remifentanil injection solution to be obtained by diluting the colorant-containing remifentanil injection solution formulation with the diluting solution from a colorless injection solution by visual observation. Thereby it is possible to prevent the occurrence of medical malpractice of erroneously injecting the diluting solution not containing the remifentanil (diluting solution before it is mixed with the remifentanil injection solution formulation) to a patient at an anesthetizing time.

(1) In a remifentanil injection solution formulation of the present invention containing remifentanil and/or physiologically acceptable salts thereof, water, and a stabilizer, said remifentanil injection solution formulation contains said water at a rate of 0.007 to 0.025 mL per 1 mg of said remifentanil.

(2) In a remifentanil injection solution formulation of the present invention containing remifentanil and/or physiologically acceptable salts thereof, ethanol, and a stabilizer, said remifentanil injection solution formulation contains said ethanol at a rate of 0.10 to 0.50 mL per 1 mg of said remifentanil.

(3) In a remifentanil injection solution formulation according to the above (1) or (2), said stabilizer is polyethylene glycol.

(4) In a remifentanil injection solution formulation according to the above (1) or (3), a content ratio between said water and said stabilizer is set to 2:23 to 2:198 in a volume ratio.

(5) In a remifentanil injection solution formulation according to the above (2) or (3), a content ratio between said ethanol and said stabilizer is set to 3:2 to 3:7 in a volume ratio.

(6) In a remifentanil injection solution formulation according to any one of the above (1) through (5), as a content of said remifentanil and/or said physiologically acceptable salts thereof to be contained in said remifentanil injection solution formulation, 1 to 10 mg of said remifentanil is contained in said remifentanil injection solution formulation per 1 mL thereof.

(7) A remifentanil injection solution formulation according to any one of the above (1) through (6) contains a colorant.

The invention claimed is:

1. A remifentanil injection solution formulation comprising
water, a stabilizer and remifentanil and/or physiologically acceptable salts thereof,
wherein said stabilizer is polyethylene glycol or propylene glycol,
said remifentanil injection solution formulation contains said water at a rate of 0.007 to 0.025 mL per 1 mg of said remifentanil, and
a content ratio between said water and said stabilizer is set to 2:23 to 2:198 in a volume ratio.

2. A remifentanil injection solution formulation according to claim 1, as a content of said remifentanil and/or said physiologically acceptable salts thereof to be contained in said remifentanil injection solution formulation, 1 to 10 mg of said remifentanil is contained in said remifentanil injection solution formulation per 1 mL thereof.

3. A remifentanil injection solution formulation according to claim 1, wherein said remifentanil injection solution formulation has a survival rate of remifentanil not less than 95% after the remifentanil injection solution formulation was stored at 60 degrees C. for one week.

4. A remifentanil injection solution formulation according to claim 1, wherein said stabilizer is polyethylene glycol, said remifentanil and/or physiologically acceptable salts thereof is remifentanil hydrochloride, said remifentanil injection solution formulation contains said water at a rate of 0.007 to 0.025 mL per 1 mg of said remifentanil hydrochloride, and a content ratio between said water and said polyethylene glycol is set to 2:23 to 2:198 in a volume ratio.

5. A remifentanil injection solution formulation according to claim 1, wherein said remifentanil injection solution formulation contains a colorant.

6. A prefilled syringe filled a remifentanil injection solution formulation and subjected to high-pressure steam sterilization,
wherein said remifentanil injection solution formulation comprises water, a stabilizer and remifentanil and/or physiologically acceptable salts thereof,
said stabilizer is polyethylene glycol or propylene glycol,
said remifentanil injection solution formulation contains said water at a rate of 0.007 to 0.025 mL per 1 mg of said remifentanil, and
a content ratio between said water and said stabilizer is set to 2:23 to 2:198 in a volume ratio.

7. A prefilled syringe according to claim 6, wherein said prefilled syringe comprises a gasket made of butyl rubber and syringe body made of cyclic polyolefin.

8. A prefilled syringe according to claim 7, wherein said syringe body has a capacity of 1 mL.

* * * * *